US009488572B2

(12) United States Patent
Sertel et al.

(10) Patent No.: US 9,488,572 B2
(45) Date of Patent: Nov. 8, 2016

(54) NON-CONTACT PROBE MEASUREMENT TEST BED FOR MILLIMETER WAVE AND TERAHERTZ CIRCUITS, INTEGRATED DEVICES/COMPONENTS, SYSTEMS FOR SPECTROSCOPY USING SUB-WAVELENGTH-SIZE-SAMPLES

(71) Applicant: OHIO STATE INNOVATION FOUNDATION, Columbus, OH (US)

(72) Inventors: Kubilay Sertel, Hillard, OH (US); Cosan Caglayan, Columbus, OH (US); Georgios Trichopoulos, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 14/309,432

(22) Filed: Jun. 19, 2014

(65) Prior Publication Data
US 2015/0102225 A1 Apr. 16, 2015

Related U.S. Application Data

(60) Provisional application No. 61/836,954, filed on Jun. 19, 2013.

(51) Int. Cl.
*G01N 21/35* (2014.01)
*G01N 21/3581* (2014.01)
*G01R 31/28* (2006.01)

(52) U.S. Cl.
CPC ....... *G01N 21/3581* (2013.01); *G01R 31/2822* (2013.01)

(58) Field of Classification Search
CPC .................................................. G01N 21/35
See application file for complete search history.

(56) References Cited

U.S. PATENT DOCUMENTS

| 6,759,863 | B2 | 7/2004 | Moore | |
|---|---|---|---|---|
| 6,885,202 | B2 | 4/2005 | Slupsky | |
| 2006/0085160 | A1* | 4/2006 | Ouchi | 702/150 |
| 2007/0252992 | A1* | 11/2007 | Itsuji | 356/369 |
| 2013/0222571 | A1* | 8/2013 | Kychakoff et al. | 348/82 |

OTHER PUBLICATIONS

Su, et al., "Sb-Heterostructure millimeter-wave detectors with reduced capacitance and noise equivalent power," IEEE Electron Device Letters, vol. 29, No. 6 pp. 536-539 (Jun. 2008).

(Continued)

*Primary Examiner* — David Porta
*Assistant Examiner* — Hugh H Maupin
(74) *Attorney, Agent, or Firm* — Fay Sharpe LLP

(57) ABSTRACT

A test fixture for characterizing a device-under-test (DUT) includes first and second planar antennas and a planar waveguide arranged to guide terahertz (THz) and/or millimeter wave (mmW) radiation between the first and second planar antennas. The planar waveguide is further configured to couple THz and/or mmW radiation guided between the first and second planar antennas with the DUT. A beam forming apparatus is arranged to transmit a probe THz and/or mmW radiation beam to the first planar antenna of the test fixture. An electronic analyzer is configured to wirelessly receive a THz and/or mmW signal emitted by the second planar antenna responsive to transmission of the probe THz and/or mmW radiation beam to the first planar antenna. The planar antennas may be asymmetrical beam-tilted slot antennas.

27 Claims, 8 Drawing Sheets

(56) References Cited

OTHER PUBLICATIONS

Dyakonov, et al., "Plasma wave electronics: Novel Terahertz devices using two dimensional electron fluid," IEEE Trans. Electron Devices, vol. 43, pp. 1640-1645 (Oct. 1996).

Knap, et al., "Nonresonant detection of Terahertz radiation in field effect transistors," Journal of Applied Physics, vol. 91, pp. 9346-9353 (2002).

Williams, et al., "3.4-THz quantum cascade laser based on longitudinal-optical-phonon scattering for depopulation," Applied Physics Letters, vol. 82, pp. 1015-1017 (2003).

Topalli, et al., "An Indirect Impedance Characterization Method for Monolithic THz Antennas Using Coplanar Probe Measurements," IEEE Antennas and Wireless Propagation Letters, vol. 11, pp. 3-5 (Dec. 2011).

Trichopoulos, et al., "A Broadband Focal plane Array Camera for Real-time THz Imaging Applications," IEEE Transactions on Antennas and Propagation, pp. 1733-1740 (Jan. 25, 2013).

Topalli, et al., "Non-contact probes for THz circuits and integrated devices," In Antennas and Propagation Society International Symposium (APSURSI), 2012 IEEE, pp. 1-2 (Jul. 2012).

Trichopoulos, et al., "Non-contact THz probes for on-chip device and IC characterization." In Aerospace and Electronics Conference (NAECON), 2012 IEEE National, pp. 34-35. (Jul. 25-27, 2012).

Caglayan, et al., "Device characterization with non-contact probes in the THz band." In Radio Science Meeting (USNC-URSI NRSM), 2013 US National Committee of URSI National, pp. 1-1 (Jan. 9-12, 2013).

Trichopoulos, et al., "A Novel Approach for Improving Off-Axis Pixel Performance of Terahertz Focal Plane Arrays," IEEE Transactions on Microwave Theory and Techniques, vol. 58, No. 7 pp. 2014-2021(Jul. 2010).

Filipovic, et al., "Off-Axis Properties of Silicon and Quartz Dielectric Lens Antennas," IEEE Transactions on Antennas and Propagation, vol. 45, No. 5, pp. 760-766 (May 1997).

* cited by examiner

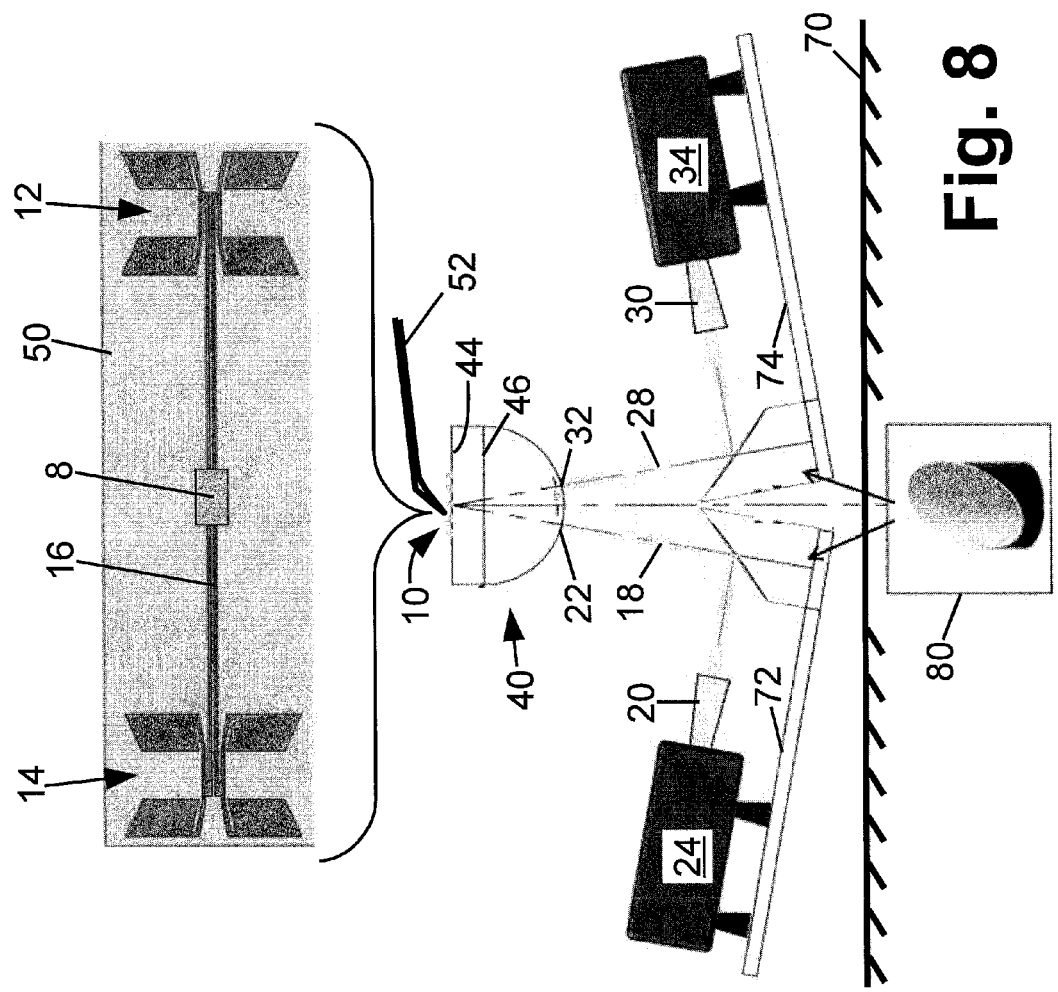

NON-CONTACT PROBE MEASUREMENT TEST BED FOR MILLIMETER WAVE AND TERAHERTZ CIRCUITS, INTEGRATED DEVICES/COMPONENTS, SYSTEMS FOR SPECTROSCOPY USING SUB-WAVELENGTH-SIZE-SAMPLES

This application claims the benefit of U.S. Provisional Application No. 61/836,954 filed Jun. 19, 2013. U.S. Provisional Application No. 61/836,954 filed Jun. 19, 2013 is incorporated by reference herein in its entirety.

This invention was made with Government support under Office of Naval Research Multidisciplinary University Research Initiative (ONR MURI) grant/contract no. N00014-11-1-0077, awarded by the Office of Naval Research (ONR). The government has certain rights in the invention.

BACKGROUND

The following relates to the millimeter or submillimeter, or equivalently extremely high frequency (EHF) to terahertz (THz), device characterization arts, millimeter to submillimeter (EHF to THz) device spectroscopy arts, millimeter or submillimeter (EHF or THz) device probe arts, and the like.

The International Telecommunication Union (ITU) designates the frequency range 0.3 THz to 3 THz (where 1 THz=$10^{12}$ Hz) as terahertz radiation, terahertz waves, or tremendously high frequency radiation. The terahertz radiation range can alternatively be written as the wavelength range 1 mm to 0.1 mm (or 100 micron), and hence the terahertz radiation range is also called submillimeter radiation, and is in the 0.1 mm to 1 mm range. The frequency range 30-300 GHz frequency range (1-10 mm wavelength range) is known as the Extremely High Frequency (EHF) or millimeter band, sometimes abbreviated as the "mmW" band. Thus, mmW radiation is in the 1 mm to 10 mm range. Sensor, transceiver, spectroscopy and communications systems, and the like electronic and photonic systems for the THz and mmW bands are distinctly different in technology and science as compared to lower frequency bands of the electromagnetic spectrum. Much like the infrared and optical frequency bands are separately addressed due to the aforementioned technological and scientific differences, the mmW and THz bands are also distinct from the rest of the radio frequency spectrum.

Recent advances in novel THz devices that exploit ultrafast quantum mechanical transitions in semiconductor systems (such as tunneling, plasma waves and so forth) are enabling new sensors for the THz band. New devices, such as heterostructure backward diodes (HBDs), 2D electron gas (2DEG) field effect transistors (FETs), high electron mobility transistors (HEMTs), metal-insulator-insulator-metal (MIIM) junctions and quantum cascade structures can be produced with cutoff frequencies well beyond 1 THz. In order to minimize parasitics and enable ultrafast operation, these devices typically have dimensions in the micrometer to nanometer scale. Such high speed devices are typically characterized in the millimeter wave (mmW) regime by contact probes. However, for the sub-millimeter or THz bands such probes are not readily available. For example, focal plane array antennas feature very small details that do not allow direct probe contact for input impedance characterization. Alternatively, indirect impedance characterization methods have been developed in order to characterize THz antennas.

BRIEF DESCRIPTION

In some illustrative embodiments disclosed as illustrative examples herein, an apparatus for performing terahertz (THz) or millimeter wave (mmW) characterization of an associated device-under-test (DUT) is disclosed. The apparatus comprises: a test fixture including first and second planar antennas and a planar waveguide arranged to guide THz or mmW radiation between the first and second planar antennas and further configured to couple THz or mmW radiation guided between the first and second planar antennas with the associated DUT; a beam forming apparatus arranged to transmit a probe THz or mmW radiation beam to the first planar antenna of the test fixture; and an electronic analyzer configured to wirelessly receive a THz or mmW signal emitted by the second planar antenna responsive to transmission of the probe THz or mmW radiation beam to the first planar antenna.

In some illustrative embodiments disclosed as illustrative examples herein, an apparatus is disclosed for performing characterization of an associated device-under-test (DUT) fabricated as a component of a test fixture that further includes first and second planar antennas and a planar waveguide connecting the first and second planar antennas with the DUT. The apparatus comprises: a beam forming apparatus configured to wirelessly transmit a probe THz or mmW radiation beam to the first planar antenna of the test fixture; a signal receiver configured to wirelessly receive a THz or mmW signal emitted by the second planar antenna in response to receipt of the probe THz or mmW radiation beam at the first planar antenna; and an electronic analyzer in wired connection with the signal receiver and configured to perform at least one of vector network analysis and spectroscopic analysis of the THz or mmW signal wirelessly received by the signal receiver.

In some illustrative embodiments disclosed as illustrative examples herein, an apparatus comprises an integrated circuit including a THz or mmW device under test (DUT), first and second planar antennas, and a planar waveguide arranged to guide THz or mmW radiation between the first and second planar antennas and further configured to couple THz or mmW radiation guided between the first and second planar antennas with the THz or mmW DUT. The apparatus may further comprise an electronic analyzer wirelessly connected with the THz or mmW DUT by wireless contacts comprising the first and second planar antennas.

In some illustrative embodiments disclosed as illustrative examples herein, a method is disclosed for characterizing a device-under-test (DUT). The method comprises: providing a test fixture including first and second planar antennas connected via the terahertz DUT; wirelessly transmitting probe THz or mmW radiation to the first planar antenna of the test fixture; and wirelessly receiving a THz or mmW signal characterizing the DUT which is emitted by the second planar antenna of the test fixture responsive to the transmitting. In some embodiments the analyzing of the received terahertz signal uses a vector network analyzer (VNA). In some embodiments the analyzing comprises performing spectroscopic analysis on the received THz or mmW signal. The providing operation may comprise monolithically fabricating on a substrate wafer or chip the DUT, the first and second planar antennas, and a waveguide connecting the first planar antenna and the second planar antenna with the DUT.

BRIEF DESCRIPTION OF THE DRAWINGS

Unless otherwise noted, the drawings are not to scale or proportion. The drawings are provided only for purposes of illustrating preferred embodiments and are not to be construed as limiting.

FIG. 8 diagrammatically shows a variant apparatus for performing terahertz characterization of a DUT.

DETAILED DESCRIPTION OF PREFERRED EMBODIMENTS

Disclosed herein are test beds and testing techniques for device and circuit testing at THz and mmW frequencies without the need to make electrical contact to convey electromagnetic signals. In some embodiments, the disclosed non-contact probe design includes beam-tilted THz and/or mmW antennas integrated into the coplanar environment of monolithic circuits and devices, such as high-speed transistors, diodes and integrated circuits. In some illustrative embodiments, a commercially available THz and/or mmW vector network analyzer (VNA) (with extension modules) and waveguide-fed horn antennas are used to excite the beam-tilted planar THz and/or mmW antennas integrated into the test device feed lines. In some embodiments, an extended hemispherical lens configuration is used to enhance THz and/or mmW coupling efficiency. Propagation effects and the antenna coupling artifacts are optionally removed using a conventional calibration method using several known loads (for example, a standard and short circuit loads).

Figure 1:
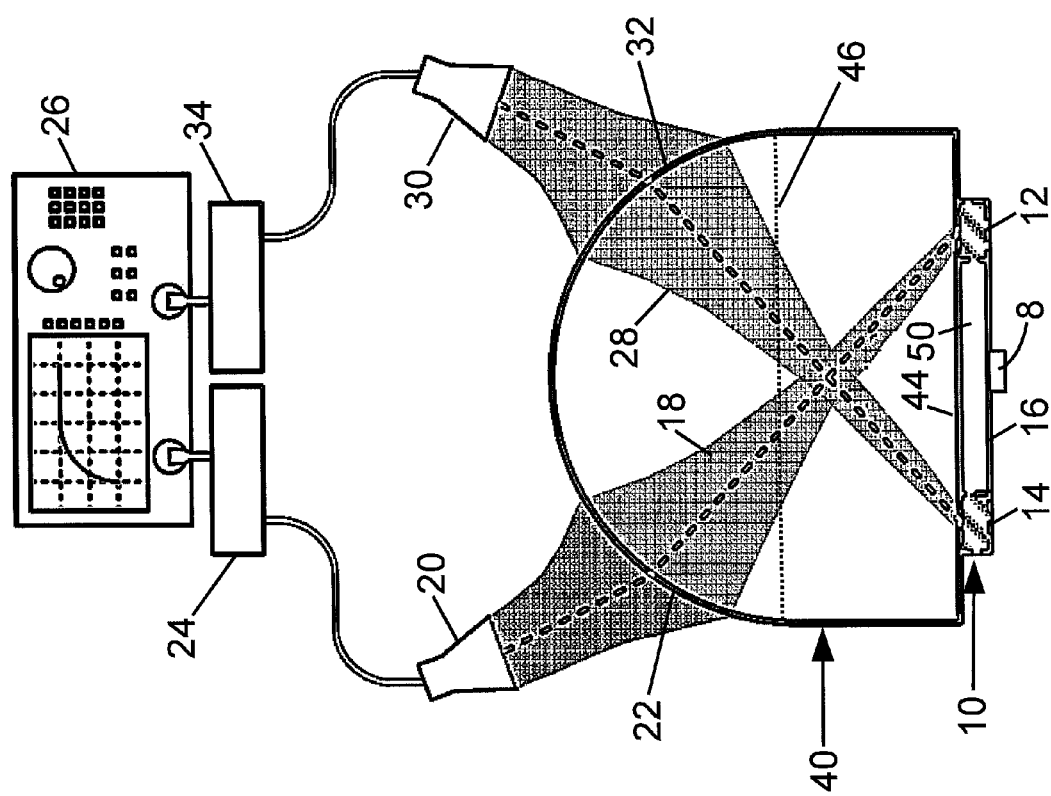
FIG. 1 diagrammatically shows an illustrative apparatus for performing terahertz characterization of a device-under-test (DUT).

With reference to FIG. 1, an illustrative apparatus for performing THz and/or mmW characterization of a device-under-test (DUT) 8 is described. The DUT 8 may, by way of non-limiting illustrative example, comprise a heterostructure backward diode (HBD), a two-dimensional electron gas (2DEG) field effect transistor (FET), a high electron mobility transistor (HEMT), a metal-insulator-insulator-metal (MIIM) junction, a quantum cascade structure, an integrated circuit such as a low noise amplifier, a power amplifier, a THz and/or mmW mixer, a THz and/or mmW sensor, or so forth. Such devices can be produced with cutoff frequencies well beyond 1 THz. See, e.g. Rajavel et al., "Sb-Heterostructure millimeter-wave detectors with reduced capacitance and noise equivalent power," *IEEE Electron Device Letters*, vol. 29, no. 6, June 2008; Dyakonov et al., "Plasma wave electronics: Novel Terahertz devices using two dimensional electron fluid," IEEE Trans. Electron Devices, vol. 43, p. 1640-1645, October 1996; Knap et al., "Nonresonant detection of Terahertz radiation in field effect transistors", *J. Appl. Phys.*, vol. 91, pp. 9346-9353, 2002; Williams et al., "3.4-THz quantum cascade laser based on longitudinal-optical-phonon scattering for depopulation", *Appl. Phys. Lett.*, vol. 82, pp. 1015-1017, 2003. The DUT 8 is mounted on, or fabricated as part of, a test fixture 10, which is a device or setup designed to hold the DUT 8 in place and allow it to be tested by being subjected to controlled electronic test signals. The illustrative test fixture 10 includes, a first planar antenna 12, a second planar antenna 14, and a planar waveguide 16 arranged to guide THz and/or mmW radiation between the first and second planar antennas 12, 14. The planar waveguide 16 is further configured to couple THz and/or mmW radiation guided between the first and second planar antennas 12, 14 with the DUT 8. A THz and/or mmW beam forming apparatus is arranged to transmit a probe THz and/or mmW radiation beam 18 to the first planar antenna 12 of the test fixture 10. In the illustrative example of FIG. 1, the THz beam forming apparatus includes a THz and/or mmW radiator, such as an illustrative horn antenna 20 (or alternatively a broadband, quasi-optical, photoconductive-switch-based THz and/or mmW radiator synchronized by a femto-second pulsed laser, or another THz and/or mmW radiator), and a lens 22 focusing THz and/or mmW radiation from the THz and/or mmW radiator 20 onto the first planar antenna 12 of the test fixture 10 to form the probe THz and/or mmW radiation beam 18. In the illustrative example, the probe signal is generated by a THz and/or mmW frequency extension module 24 operatively connected with a THz and/or mmW vector network analyzer (VNA) 26.

An electronic analyzer, such as the illustrative THz and/or mmW VNA 26, or a spectrum analyzer, or a power detector (Golay cell or a THz pyroelectric sensor), or so forth, is configured to wirelessly receive a THz and/or mmW signal 28 emitted by the second planar antenna 14 responsive to transmission of the probe THz and/or mmW radiation beam 18 to the first planar antenna 12. In the illustrative embodiment of FIG. 1, a THz and/or mmW receiver 30, such as an illustrative horn antenna, is operatively coupled with the electronic analyzer 26, and a receiving lens 32 conveys the THz and/or mmW signal 28 emitted by the second planar antenna 14 to the THz and/or mmW receiver 30. A second THz and/or mmW frequency extension module 34 is operatively connected with the THz and/or mmW VNA 26 to input the received THz and/or mmW signal to the VNA 26.

In the illustrative example of FIG. 1, the lenses 22, 32 are constructed as a unitary lens 40 that defines the lens surface 22 configured to focus the probe THz and/or mmW radiation beam 18 onto the first planar antenna 12, and that defines the lens surface 32 wirelessly coupling the THz and/or mmW signal 28 emitted by the second planar antenna 14 to the THz and/or mmW signal receiver 30. In the illustrative embodiment the unitary lens 40 comprises a hemispherical lens defining the lens surfaces 22, 32 and further having a planar back side 44 on which the test fixture 10 is disposed. The illustrative unitary lens 40 may also be referred to as an extended hemispherical lens as it includes a hemispherical portion and an extension portion meeting the hemispherical portion at a junction diagrammatically denoted by a dotted line 46 in FIG. 1. As seen in FIG. 1, in this illustrative embodiment the wireless path from the first lens surface 22 to the first planar antenna 12 is contained in the unitary lens 40, and the wireless path from the second planar antenna 14 to the second lens surface 32 is also contained in the unitary lens 40. In practice, the two lens surfaces 22, 32 overlap significantly. This illustrative embodiment reduces signal losses at interfaces between different materials and enables efficient coupling of the wireless THz and/or mmW signals onto the planar antennas of the text fixture.

Figure 2:
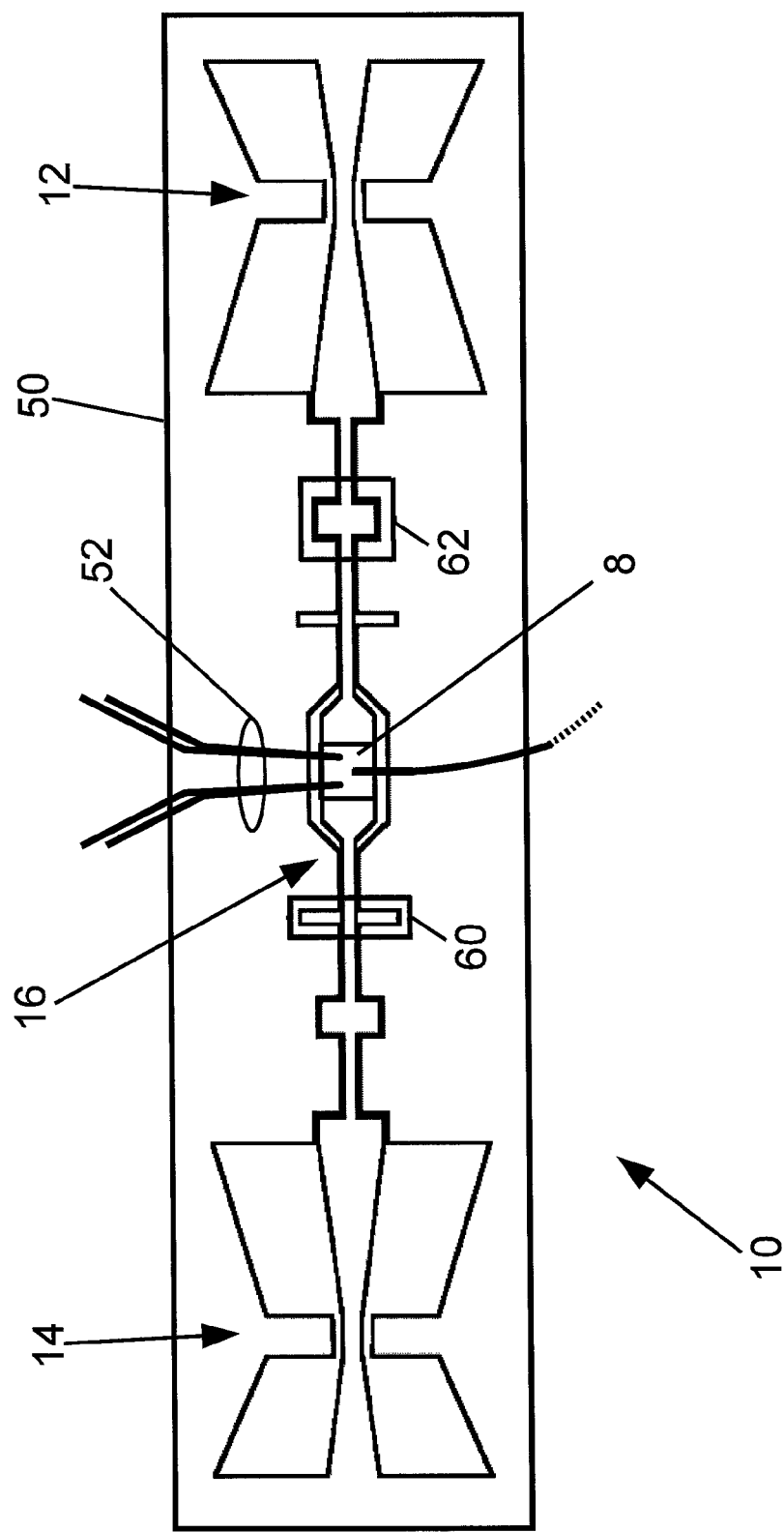
FIG. 2 diagrammatically shows a plan view of the test fixture of FIG. 1.

With continuing reference to FIG. 1 and with further reference to FIG. 2 which diagrammatically shows a plan view of the test fixture 10, the first and second planar antennas 12, 14 are suitably constructed as first and second asymmetrical beam-tilted slot antennas, such as the illustrative asymmetrical beam-tilted double slot antennas. The test fixture 10 includes (or, viewed alternatively, is supported by) a substrate wafer or chip 50 on which the various components 12, 14, 16 are fabricated. The substrate wafer or chip 50 supporting the various components 12, 14, 16 may, for example, comprise GaAs or high resistivity (high-res) silicon or GaN or InP, although other THz and/or mmW-compliant substrate materials are contemplated. In some embodiments, the DUT 8 is also fabricated on the same substrate wafer or chip 50 on which the various components 12, 14, 16 are fabricated. In such an embodiment, the test fixture 10 is an integrated circuit including (in this embodiment) the components 12, 14, 16 and the DUT 8, suitably formed by monolithically fabricating on the substrate wafer or chip 50 the DUT 8, the first and second planar antennas 12, 14, and a waveguide 16 connecting the first planar antenna 12 and the second planar antenna 14 with the DUT 8.

As previously mentioned, in the illustrative embodiment of FIG. 1 the test fixture 10 is disposed on the planar back side 44 of the unitary lens 40. More particularly, as seen in FIG. 1, in this illustrative embodiment the substrate wafer or chip 50 of the test fixture 10 is disposed on the planar second side of the unitary lens 40. This allows the DUT 8 to be accessed, for example to apply an optional DC bias. The disclosed THz and/or mmW test bed is wireless in that no wired connections are used to inject or receive THz and/or mmW signals. However, it is contemplated to employ a wired DC bias connection to the DUT 8, such as wire bonds or, in the illustrative example of FIG. 2, DC probes 52 that are configured to contact the DUT 8 to apply a DC bias to the DUT 8.

The THz and/or mmW test bed of illustrative FIG. 1 effectively couples the transmitted THz and/or mmW power into and out of the DUT 8. The transmitting and receiving beams of the horn antennas 20, 30 are effectively coupled into the hemispherical lens 40, and focused onto the device plane using an the off-axis excitation. See Filipovic et al., "Off-axis properties of silicon and quartz dielectric lens antennas", IEEE Trans. Microwave Theory and Tech., vol. 45, no. 5, pp. 760-766, May 1997; Trichopoulos et al., "A novel approach for improving off-axis pixel performance of THz focal plane arrays," *IEEE Trans. Microw. Theory & Tech*, vol. 58, no. 7, pp. 2014-2021, July 2010. The two additional planar THz and/or mmW antennas 12, 14 are provided to couple the THz and/or mmW radiation into the test device ports. The planar THz and/or mmW antennas 12, 14 are designed to transmit and receive from the same off-axis directions as the external horns 20, 30 that are coupled with the ports of the VNA 26. As discussed Trichopoulos et al., supra, the design flexibility afforded by the double slot antennas (see Filipovic et al., supra) allows for the desired beam-corrected/beam-tilted broadband operation, which enhances the coupling efficiency (by more than 10 dB).

With particular reference to FIG. 2, the planar waveguide 16 is suitably a co-planar waveguide (CPW), and the planar THz and/or mmW antennas 12, 14 are suitably broadband double slot antenna having a "butterfly" shaped slot design, as described in Topalli et al., "An indirect impedance characterization method for monolithic THz antennas," in *IEEE Int. Symposium on Antennas and Propagation*, pp. 1882-1884, July 2011. The two asymmetrical beam-tilted butterfly slot antennas 12, 14 can be integrated into the CPW environment, yielding a flexible topology that allows for the optional integration of matching circuitry (to optimize device response) into the CPW 16, along with DC biasing connections (e.g. the DC probes 52). Various standard active and passive circuits, such as filters and matching networks, can also be integrated using this topology. For example, the test fixture 10 of illustrative FIG. 2 includes a high impedance inductive line 60 and a low-impedance capacitive line 62.

Figure 3:
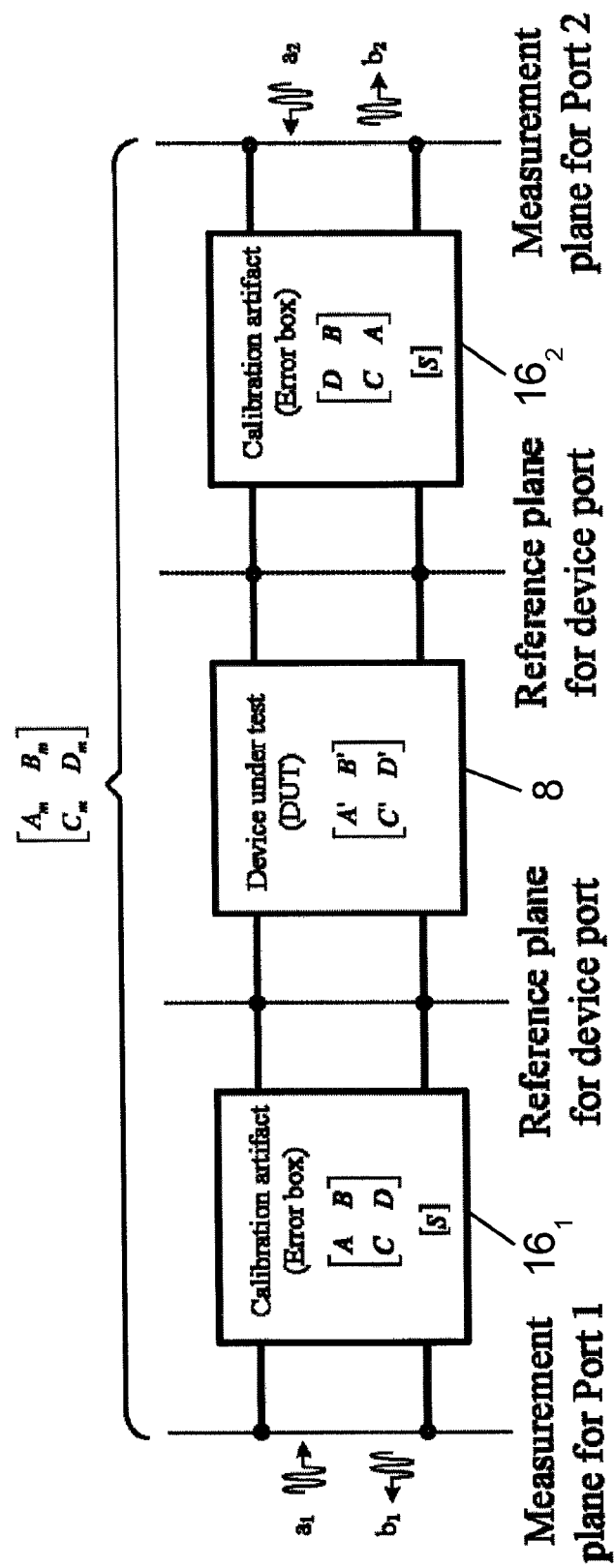
FIG. 3 shows a two-port network model of the test fixture of FIG. 1.
Figure 4:
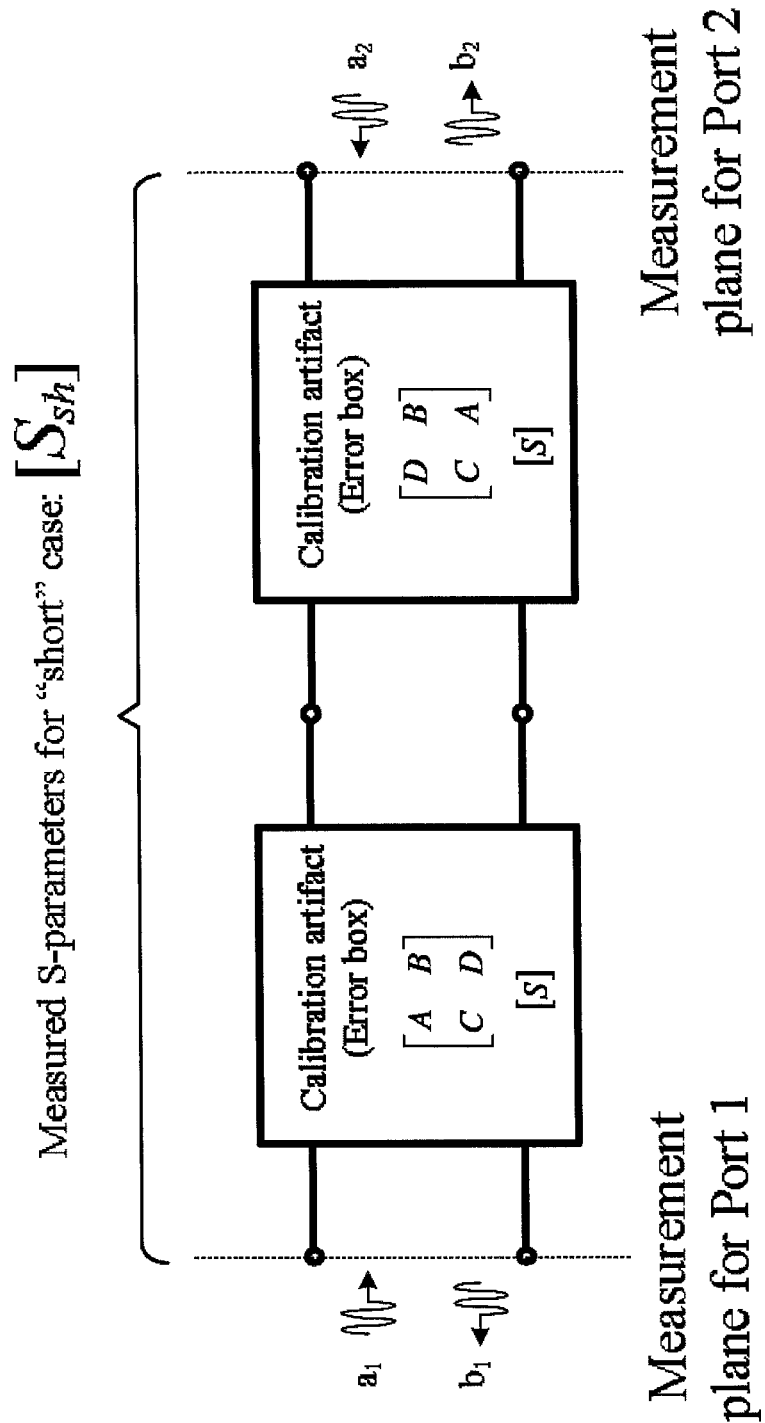
FIG. 4 shows a two-port network model of the test fixture of FIGS. 2 and 3 with the DUT replaced by a short circuit.
Figure 5:
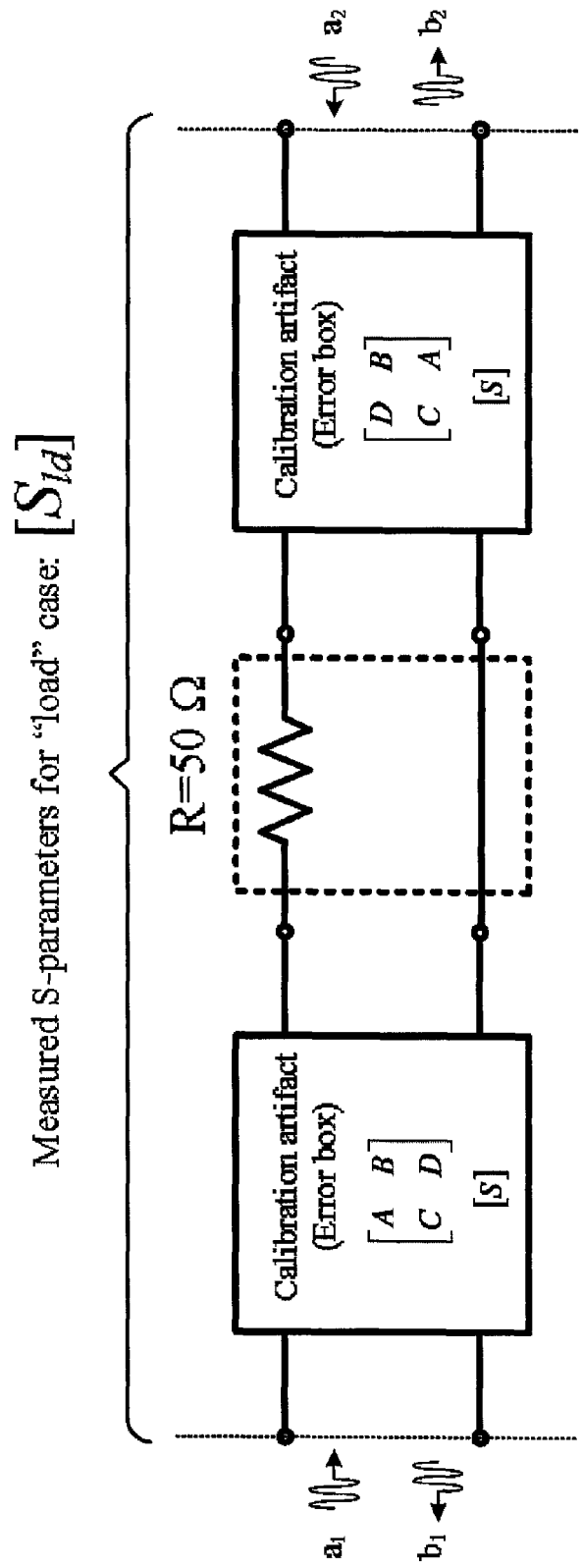
FIG. 5 shows a two-port network model of the test fixture of FIGS. 2 and 3 with the DUT replaced by a standard load (50 ohm resistor).

With reference to FIGS. 3-5, calibration and initial validation of the disclosed non-contact THz and mmW probe is described. FIG. 3 illustrates a two-port network model of the measurement path of the test fixture 10. The DUT 8 is modeled by a matrix $$\begin{bmatrix} A' & B' \\ C' & D' \end{bmatrix}.$$

The "Measurement plane for Port 1" designates the connection of the first planar antenna 12 to the waveguide 16, while the "Measurement plane for Port 2" designates the connection of the second planar antenna 14 to the waveguide 16. The measurement path from the first planar antenna 12 to the DUT 8 is characterized by a matrix $16_1$ which in the illustrative two-port network model is represented by a matrix $$\begin{bmatrix} A & B \\ C & D \end{bmatrix}.$$

The measurement path from the DUT 8 to the second planar antenna 14 is characterized by a matrix $16_2$ which in the illustrative two-port network model is represented by a matrix $$\begin{bmatrix} D & B \\ C & A \end{bmatrix}.$$

The measured S-parameters for the test fixture 10 including the DUT 8 are suitably represented by a matrix $$\begin{bmatrix} A_m & B_m \\ C_m & D_m \end{bmatrix}.$$

FIG. 4 illustrates the two-port network model for a short circuit fixture which is the same as the test fixture 10 of FIG. 2, except that the DUT 8 is replaced by a short circuit. The measured S-parameters for the short circuit fixture are suitably represented by a matrix $[S_{sh}]$. FIG. 5 illustrates the two-port network model for a standard load fixture which is the same as the test fixture 10 of FIG. 2, except that the DUT 8 is replaced by a standard load (namely a 50-ohm resistance in the illustrative standard load fixture of FIG. 5). The measured S-parameters for the standard load are suitably represented by a matrix $[S_{ld}]$.

For an accurate device characterization, the repeatable artifacts introduced by the probes are preferably eliminated from the measurements, and the reference planes moved to the device terminals. As shown in FIGS. 3-5, the two-port calibration artifact (or the error box) between the VNA 26 and the DUT 8 can be characterized using two separate measurements, e.g. by replacing the DUT 8 with a short (the short circuit text fixture of FIG. 4) and by replacing the DUT 8 with a known, i.e. standard, load termination (a 50 ohm resistive load in illustrative FIG. 5). After the test device measurement is taken (that is, the S-parameters $$\begin{bmatrix} A_m & B_m \\ C_m & D_m \end{bmatrix}$$

acquired using the contactless test bed and the VNA 26), the calibration artifacts are de-embedded using the short measurement $[S_{sh}]$ and the standard load measurement $[S_{ld}]$ to obtain the corrected device characteristics.

Figure 6:
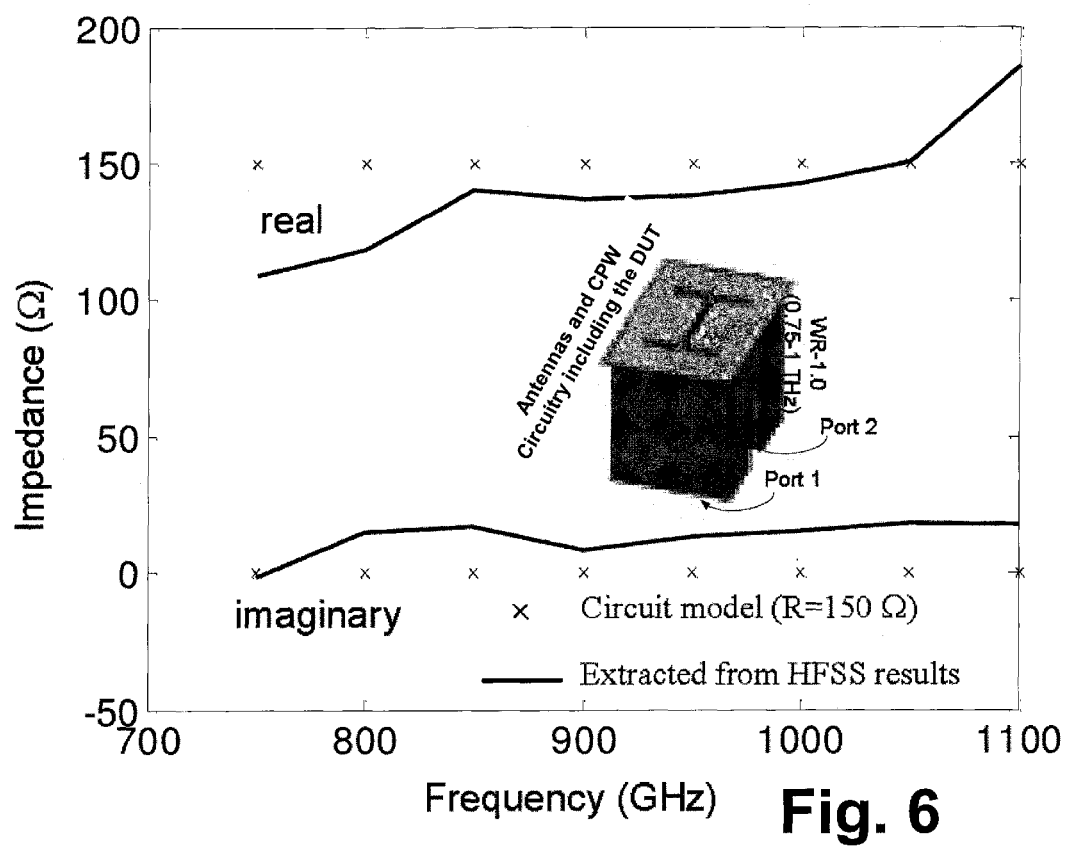
FIGS. 6 and 7 present experimental results for characterizing a 150 ohm resistor using the contactless test bed of FIG. 1.
Figure 7:
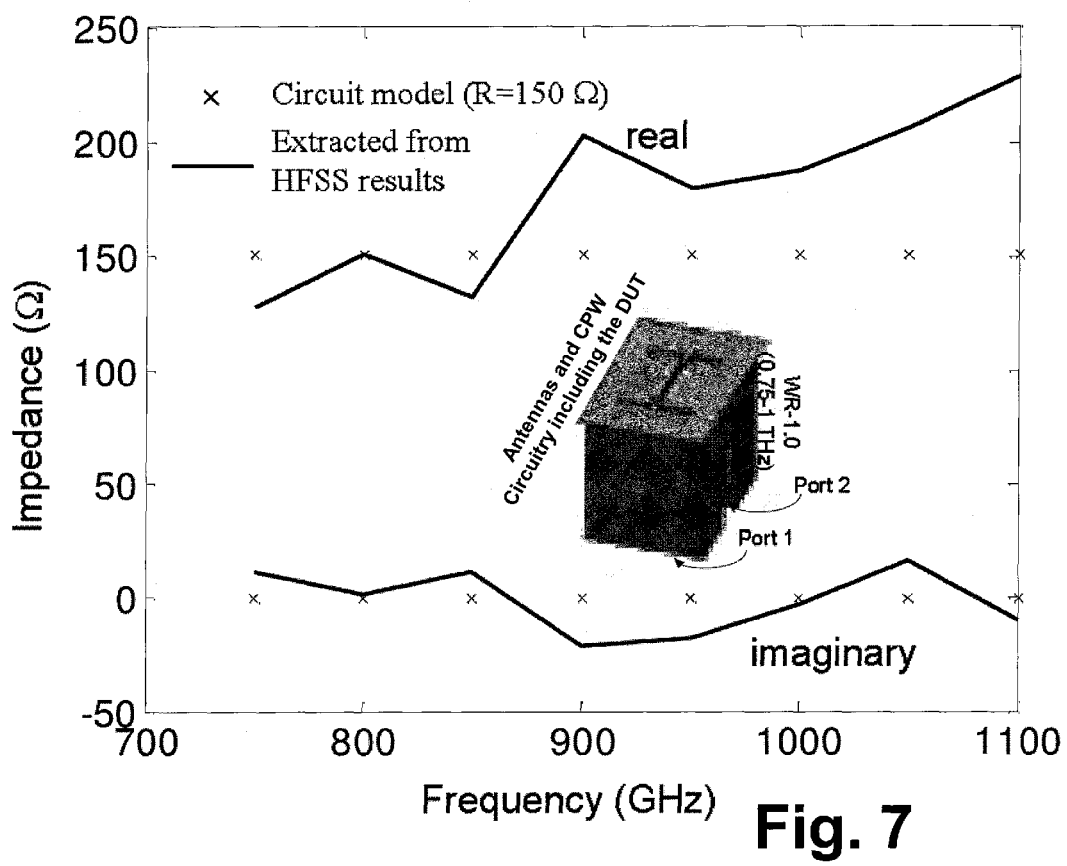

With reference to FIGS. 6 and 7, computer simulations were performed using the calibration approach outlined in FIGS. 3-5, and initial results are summarized for the non-contact THz and mmW characterization approach. For this purpose, a simplified test device comprising a 150 ohm resistor was integrated into a simplified CPW setup. For these simulations, the contactless test bed did not include the hemispherical lens 40, as diagrammatically shown in the inset of each of FIGS. 6 and 7. Open-ended THz waveguides were used to couple into the two slot dipole antennas attached to the device ports. FIG. 6 shows results for a design for a 0.9 THz to 1 THz band, while FIG. 7 shows results for a design for a 750 GHz to 850 GHz. As seen in FIG. 6, the extracted test device impedances show a fairly good agreement for two separate designs for in the 0.750-1 THz band.

With reference to FIG. 8, another THz characterization system is shown, which is similar to that of FIG. 1 and includes the THz probes 24, 34 connected to a VNA (not shown in FIG. 8, but suitably connected to the VNA 26 as shown in FIG. 1), spectrum analyzer, or other electronic analyzer which is used to characterize the DUT 8 in the test fixture 10 as described with reference to FIGS. 1 and 2. The THz and/or mmW characterization system of FIG. 8 also includes the horn antenna 20, 30 and unitary lens 40 of the system of FIG. 1, but in a different physical arrangement. In the arrangement of FIG. 8, the horn antenna (or, more generally, THz and/or mmW radiator) 20 is integrally constructed with the THz and/or mmW probe 24, and likewise the horn antennal (or, more generally, THz and/or mmW receiver) 30 is integrally constructed with the THz and/or mmW probe 34. These components are mounted on an optical table surface 70, optionally on angled supports 72, 74 as shown in FIG. 8. Suitable optics, such as illustrative off-axis parabolic mirrors 80 designed to redirect the THz and/or mmW beam by 90°, are used to direct probe THz radiation into the lens 22 focusing THz and/or mmW radiation from the THz and/or mmW radiator 20 onto the first planar antenna 12 of the test fixture 10 to form the probe THz and/or mmW radiation beam 18, and to direct the THz and/or mmW signal 28 emitted by the second planar antenna 14 from the receiving lens 32 to the THz and/or mmW receiver 30. In the arrangement shown in FIG. 8, the unitary lens 40 is "upside-down" as compared with its orientation in FIG. 1, so that the planar back side 44 of the unitary lens 40 is facing "upward" to form a flat surface on which the test fixture 10 is suitably disposed. This advantageously enables the DC probes 52 to be oriented to contact a flat "upper" surface of the DUT 8 which can be convenient for manipulation of the DC probes 52.

As with the characterization apparatus of FIG. 1, the system of FIG. 8 provides for contactless evaluation of active devices (e.g. DUT 8) in the THz and/or mmW regime (0.03-3 THz). The test fixture includes the pair of THz and/or mmW antennas 12, 14 that are fabricated on the substrate wafer or chip 50 (for example, comprising GaAs or high-res silicon). The THz and/or mmW antennas 12, 14 that are suitably on-chip wideband impedance-matched butterfly-shaped antennas used to couple the THz and/or mmW signals onto the coplanar waveguide (CPW) 16 device environment which also includes the DUT 8. As seen in the upper inset of FIG. 8, the two complementary THz and/or mmW antennas 12, 14 function as input/output probes and are connected with the CPW 16. The mid-section of the CPW line 16 incorporates either a standard calibration load (see FIG. 5, which may be a short circuit load as per FIG. 4) or the DUT 8, and may include matching circuitry such as the illustrative matching circuitry 60, 62 shown in FIG. 2. The DUT 8 is optionally monolithically integrated in the middle of the CPW 16. The substrate wafer or chip 50 is placed under (in the configuration of FIG. 1, or on top of in the configuration of FIG. 8) the extended-hemispherical lens 40 to facilitate optical coupling to the external transmitter 20 and to the THz receiver 30. This non-contact topology utilizes the versatility of the CPW environment, and provides the option of integrating matching and stabilization circuitry. Another advantage is that the THz and/or mmW excitation and interrogation of the integrated device (e.g. test fixture 10) is facilitated by the planar THz and/or mmW antennas 12, 14 on the same substrate 50. The calibration process already described with reference to FIGS. 3-5 is suitably applied for the system of FIG. 8 as well.

As previously mentioned, the illustrative horn antennas 20, 30 can be replaced by other suitable THz and/or mmW transmitters/receivers, such as broadband, quasi-optical, photoconductive-switch-based THz radiators synchronized by femto-second pulsed lasers. Broadband butterfly-shaped antennas are suitably used as the first and second planar antennas 12, 14 to provide broad bandwidth operation. In one illustrative embodiment, suitable planar antennas 12, 14 were fabricated on a 400 um-thick GaAs wafer, although other THz and/or mmW-compliant substrates are contemplated.

The preferred embodiments have been described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An apparatus for performing terahertz (THz) or millimeter wave (mmW) characterization of an associated device-under-test (DUT), the apparatus comprising:
 a test fixture configured to hold the associated DUT, the test fixture including first and second off-axis planar antennas designed to transmit and receive along different respective first and second off-axis directions, and a planar waveguide arranged to guide THz or mmW radiation between the first and second off-axis planar antennas and further configured to couple THz or mmW radiation guided between the first and second off-axis planar antennas with the associated DUT held by the test fixture, wherein the test fixture includes no wired connection to a THz or mmW signal source;
a beam forming apparatus arranged to wirelessly transmit a probe THz or mmW beam along the first off-axis direction to the first off-axis planar antenna of the test fixture; and
a THz or mmW receiver arranged to wirelessly receive a THz or mmW signal emitted along the second off-axis direction by the second off-axis planar antenna responsive to transmission of the probe THz or mmW beam to the first off-axis planar antenna.

2. The apparatus of claim 1 further comprising:
a vector network analyzer (VNA) operatively coupled with the THz or mmW receiver.

3. The apparatus of claim 1 further comprising:
an electronic analyzer operatively coupled with the THz or mmW receiver and configured to perform spectroscopic analysis of the wirelessly received THz or mmW signal.

4. The apparatus of claim 1 wherein the first and second off-axis planar antennas are first and second asymmetrical beam-tilted slot antennas.

5. The apparatus of claim 4 wherein the first and second off-axis planar antennas are first and second asymmetrical beam-tilted double slot antennas.

6. The apparatus of claim 1 wherein the beam forming apparatus includes:
a THz or mmW radiator; and
a lens focusing THz or mmW radiation from the THz or mmW radiator onto the first off-axis planar antenna of the test fixture to form the probe THz or mmW beam.

7. The apparatus of claim 6 further comprising:
a receiving lens conveying the THz or mmW signal emitted by the second off-axis planar antenna to the THz or mmW receiver.

8. The apparatus of claim 7 wherein the THz or mmW radiator comprises a horn antenna and the THz or mmW receiver comprises a horn antenna.

9. The apparatus of claim 8 wherein the THz or mmW radiator further comprises an off-axis parabolic mirror and the THz or mmW receiver further comprises an off-axis parabolic mirror.

10. The apparatus of claim 7 comprising:
a unitary lens defining the lens focusing THz or mmW radiation from the THz or mmW radiator onto the first off-axis planar antenna and defining the receiving lens conveying the THz or mmW signal emitted by the second off-axis planar antenna to the THz or mmW receiver.

11. The apparatus of claim 10 wherein the unitary lens includes:
a hemispherical side defining the lens focusing THz or mmW radiation from the THz or mmW radiator onto the first off-axis planar antenna and defining the receiving lens conveying the THz or mmW signal emitted by the second off-axis planar antenna to the THz or mmW receiver; and
a planar back side on which the test fixture is disposed.

12. The apparatus of claim 10 wherein:
the test fixture further includes a substrate wafer or chip on which the first and second off-axis planar antennas and the planar waveguide are fabricated;
the unitary lens includes a lensing side and a planar second side; and
the substrate wafer or chip of the test fixture is disposed on the planar second side of the unitary lens.

13. The apparatus of claim 1 further comprising:
DC probes configured to contact the associated DUT to apply a DC bias to the associated DUT.

14. The apparatus of claim 1 wherein the test fixture further includes:
a substrate wafer or chip on which the first and second off-axis planar antennas and the planar waveguide are fabricated.

15. The apparatus of claim 1 wherein the test fixture comprises an integrated circuit including a substrate wafer or chip on which are fabricated the first and second off-axis planar antennas, the planar waveguide, and the associated DUT.

16. An apparatus for performing characterization of an associated device-under-test (DUT) fabricated as a component of a test fixture that further includes first and second beam-tilted planar antennas designed to transmit and receive along different respective first and second off-axis directions and a planar waveguide connecting the first and second beam-tilted planar antennas with the DUT, the apparatus comprising:
a beam forming apparatus configured to wirelessly transmit a probe terahertz (THz) or millimeter wave (mmW) radiation beam to the first beam-tilted planar antenna of the integrated circuit along the first off-axis direction;
a signal receiver configured to wirelessly receive a THz or mmW signal emitted by the second beam-tilted planar antenna along the second off-axis direction in response to receipt of the probe THz or mmW radiation beam at the first beam-tilted planar antenna along the first off-axis direction; and
an electronic analyzer in wired connection with the signal receiver and configured to perform at least one of vector network analysis and spectroscopic analysis of the THz or mmW signal wirelessly received by the signal receiver.

17. The apparatus of claim 16 wherein the electronic analyzer is configured to perform vector network analysis of the THz or mmW signal wirelessly received by the signal receiver.

18. The apparatus of claim 16 wherein the electronic analyzer is configured to perform spectroscopic analysis of the THz or mmW signal wirelessly received by the signal receiver.

19. The apparatus of claim 16 wherein the beam forming apparatus includes:
a radiator configured to emit THz or mmW radiation; and
a lens focusing THz or mmW radiation emitted by the radiator onto the first beam-tilted planar antenna of the test fixture along the first off-axis direction.

20. The apparatus of claim 16 comprising:
a unitary lens configured to focus the probe THz or mmW radiation beam onto the first beam-tilted planar antenna along the first off-axis direction and to wirelessly couple the THz or mmW signal emitted by the second beam-tilted planar antenna along the second off-axis direction to the signal receiver.

21. The apparatus of claim 16 further comprising:
DC probes configured to contact the associated DUT to apply a DC bias to the associated DUT.

22. An apparatus comprising:
an integrated circuit including:
a terahertz (THz) or millimeter wave (mmW) device under test (DUT),
first and second planar antennas, and
a planar waveguide arranged to guide THz or mmW radiation between the first and second planar antennas and further configured to couple THz or mmW radiation guided between the first and second planar antennas with the THz or mmW DUT by the planar waveguide having a first end connected with the first planar antenna, a second end connected with the second planar antenna, and the DUT connected with the planar waveguide between the first and second ends of the planar waveguide.

23. The apparatus of claim 22 further comprising:
an electronic analyzer wirelessly connected with the THz or mmW DUT by wireless contacts comprising the first and second planar antennas.

24. The apparatus of claim 23 further comprising:
DC probes configured to apply a DC bias to the THz or mmW DUT.

25. A method for characterizing a device-under-test (DUT), the method comprising:
providing a test fixture including first and second planar antennas connected via the DUT;
providing a short circuit fixture comprising the test fixture with the DUT replaced by a short circuit;
providing a standard load fixture comprising the test fixture with the DUT replaced by a standard load;
wirelessly transmitting probe THz or mmW radiation to the first planar antenna of the short circuit fixture and wirelessly receiving a short circuit signal emitted by the second planar antenna of the short circuit fixture responsive to the transmitting;
wirelessly transmitting probe THz or mmW radiation to the first planar antenna of the standard load fixture and wirelessly receiving a standard load signal emitted by the second planar antenna of the standard load fixture responsive to the transmitting;
wirelessly transmitting probe terahertz (THz) or millimeter wave (mmW) radiation to the first planar antenna of the test fixture;
wirelessly receiving a THz or mmW signal characterizing the DUT which is emitted by the second planar antenna of the test fixture responsive to the transmitting;
adjusting the THz or mmW signal characterizing the DUT based on the short circuit signal and the standard load signal to generate a calibrated THz or mmW signal characterizing the DUT; and
analyzing the calibrated THz or mmW signal characterizing the DUT using a vector network analyzer (VNA).

26. The method of claim 25 further comprising:
performing spectroscopic analysis on the received THz or mmW signal.

27. The method of claim 25 wherein the providing comprises:
monolithically fabricating on a substrate wafer or chip the DUT, the first and second planar antennas, and a waveguide connecting the first planar antenna and the second planar antenna with the DUT.

* * * * *